US006235463B1

(12) United States Patent
Critser et al.

(10) Patent No.: US 6,235,463 B1
(45) Date of Patent: May 22, 2001

(54) SORBENT METHOD FOR REMOVAL OF CRYOPROTECTANTS FROM CRYOPRESERVED ANIMAL CELLS

(75) Inventors: John K. Critser, Carmel; Erik J. Woods, Indianapolis, both of IN (US)

(73) Assignee: General Biotechnology, LLC, Carmel, IN (US)

(*) Notice: Subject to any disclaimer, the term of this patent is extended or adjusted under 35 U.S.C. 154(b) by 0 days.

(21) Appl. No.: 09/306,602

(22) Filed: May 6, 1999

Related U.S. Application Data
(60) Provisional application No. 60/085,189, filed on May 12, 1998.

(51) Int. Cl.⁷ .............................. A01N 1/02; C12N 5/00
(52) U.S. Cl. ................................. 435/2; 435/325
(58) Field of Search ........................... 435/2, 325

(56) References Cited

U.S. PATENT DOCUMENTS

| | | |
|---|---|---|
| 3,791,384 | 2/1974 | Richter et al. |
| 3,893,308 | 7/1975 | Barkay et al. |
| 4,007,087 | 2/1977 | Ericsson . |
| 4,348,283 | 9/1982 | Ash . |
| 4,429,542 | 2/1984 | Sakao et al. |
| 4,480,682 | 11/1984 | Kaneta et al. |
| 4,487,033 | 12/1984 | Sakao et al. |
| 4,581,141 | 4/1986 | Ash . |
| 4,661,246 | 4/1987 | Ash . |
| 5,277,820 | 1/1994 | Ash . |
| 5,643,794 * | 7/1997 | Liu et al. .................. 435/289.1 |
| 5,700,632 | 12/1997 | Critser et al. . |
| 6,068,775 * | 5/2000 | Custer et al. .................. 210/638 |

OTHER PUBLICATIONS

Thorner, J. and Paulus, H., "Catalytic and Allosteric Properties of Glycerol Kinase from *Escherichia coli*," Jun. 10, 1973, *J. Biol. Chem.*, vol. 248, No. 11, pp. 3922–3932.

Sherman, J.K., "Improved Methods of Preservation of Human Spermatozoa by Freezing and Freeze–Drying," *Fertility & Sterility*, vol. 14, No. 1, pp. 49–64, 1963.

Behrman, et al., "Heterologous and Homologous Inseminations with Human Semen Frozen and Stored in a Liquid–Nitrogen Freezer," *Fertility & Sterility*, vol. 17, No. 4, pp. 457–466, 1996.

Willoughby, et al., "Osmotic Tolerance Limits and Properties of Murine Spermatozoa," *Biol. of Reproduction*, vol. 55, pp. 715–727, 1996.

Gilmore, et al., "Determination of optimal cryoprotectants and procedures for their addition and removal from human spermatozoa," *Human Reproduction*, vol. 12, No. 1, pp. 112–118, 1997.

Gilmore, et al., "Effect of Cryprotectant Solutes on Water Permeability of Human Spermatozoa," *Biol. of Reproduction*, vol. 53, pp. 985–995, 1995.

Gao, et al., "Prevention of osmotic injury o human spermatozoa during addition and removal of glycerol," *Human Reproduction*, vol. 10, No. 5, pp. 1109–1122, 1995.

Gilmore, et al., "Osmotic properties of boar spermatozoa and their relevance to cryopreservation," *J. of Reproduction and Fertility*, vol. 107, pp. 87–95, 1996.

\* cited by examiner

*Primary Examiner*—Sandra E. Saucier
(74) *Attorney, Agent, or Firm*—Barnes & Thornburg

(57) ABSTRACT

A method is disclosed for removal of cryoprotectants from preserved suspension of biological cells and tissues. Sorbent materials are used, alone or in combination, to bind the cryoprotectant component of preserved cell suspensions with minimal osmotic stress on the preserved cells. The present method is used to effectively remove the cryoprotectants from cryopreserved cells and tissues prior to their use in transfusion, transplantation, insemination or other applications, with minimal osmotic damage due to cell swelling. Specific devices and methods are described.

14 Claims, 2 Drawing Sheets

SORBENT METHOD FOR REMOVAL OF CRYOPROTECTANTS FROM CRYOPRESERVED ANIMAL CELLS

This application claims benefit of Provisional Application No. 60/085,189 filed May 12, 1998.

FIELD OF INVENTION

The present invention relates to a method of removing chemical compounds used to protect cells (cryoprotectants) during low temperature preservation (cryopreservation). More particularly, this invention is directed to the use of non-toxic solid sorbents to irreversibly bind cryoprotectant compounds in cryopreserved cell suspension to remove/extract them from the suspension medium. During the cryoprotectant binding process and the concomitant reduction of cryoprotectant concentration in the cell suspension medium, intracellular cryoprotectant is osmotically drawn out of the cells and into the medium for binding to the solid sorbent.

BACKGROUND OF INVENTION

Fresh biological cells such as sperm, red blood cells, platelets and the like, are typically viable for but a short period of time in vitro. Nevertheless, it is commercially and medically significant that such cells are available for use long after they have been collected from donors, sometimes several months or even years later. Various cryopreservation methods have been developed to preserve biological cells for these relatively longer periods of time. For example, cryopreservation of sperm cells permits a domestic animal breeder to maintain stocks of valuable sperm cells for use when necessary; it enables the inexpensive transport of such stocks; and it ultimately permits genetically superior males to inseminate a larger number of females. Beyond livestock, artificial insemination is also used in human clinical medicine. As another example, cryopreservation of blood permits donated blood to be stored much longer that the typical 14 day storage period. Moreover, diseases carried in blood with a latency period longer than 14 days may not be discovered in the donor until the blood has been placed into a patient. Cryopreserved blood can be stored for a time sufficient to allow donors to be screened well beyond their date of donation.

The survivability of viable cells and tissues using prior art freezing methods is often quite low. Freezing conditions are relatively harsh and thermal shock or other phenomena such as ice crystal formation often destroy biological cells and tissues. Therefore, maximizing the viability of thawed cells and tissues has been the goal of many researchers.

The prior art discloses various methods for improving the survivability of frozen cells and tissues. In many cases, the cells are removed from their physiological milieu and suspended into artificial tissue culture media prior to preservation. U.S. Pat. No. 4,007,087 to Ericsson discloses a sperm fractionation and storage method which claims to increase the percentage of motile sperm that survive frozen storage. Ericsson discloses a method whereby motile sperm are separated from non-motile, defective or dead sperm. The fraction containing the motile sperm is then frozen. Ericsson reports this method increases the fertility of a sperm sample by enhancing the environmental (the ratio of total sperm to motile sperm) and the viability (progressiveness of motility of the motile sperm) factors affecting the fertility of a sample, but his method does not improve the population (motile sperm count) factor which is possibly most critical.

U.S. Pat No. 3,791,384 to Richter et al. discloses a method for deep freezing and thawing boar sperm which includes inactivating the fresh sperm by means of an inactivating solution that includes dextrose, dihydrate of ethylenedinitrotetraacetic acid, sodium hydrogencarbonate. Reichter reports that inactivation of the sperm gives them a greater power of resistance to freezing.

U.S. Pat. No. 4,429,542 to Sakao et al., U.S. Pat. No. 4,487,033 to Sakao et al., U.S. Pat. No. 3,893,308 to Barkay at al., and U.S. Pat. No. 4,480,682 to Kameta et al., all disclose different freezing methods which claim to improve the fertility of sperm samples. In all of these methods, the temperature of sperm in solution is lowered by various means which attempt to reduce the thermal shock and increase the survivability of the viable sperm. Most of these methods are, however, complex, cumbersome and expensive to utilize. Other freezing methods are also used including the method of rapidly freezing in liquid nitrogen vapors (Sherman J K, Improved Methods of Preservation of Humans Spermatozoa by Freezing and Freeze Drying, Fert. Steril. 14: 49–64, 1963), and the method of gradual freezing (Behrman et al., Heterologous and Homologous Insemination with Human Semen Frozen and Stored in a Liquid Nitrogen Refrigerator, Fert. Steril., 17: 457–466, 1966).

A disadvantage of the aforementioned methods resides in that low temperature preservation of the cells and tissues is accomplished by the ice crystallization process. As ice forms in the solution surrounding the cells or tissues, electrolytes and other solutes become progressively concentrated, quickly reaching concentrations which are damaging to the cells. This solute damage is attenuated by the addition of cryoprotectant chemicals such as glycerol, propylene glycol, ethylene glycol or dimethylsulfoxide. However, the cryoprotectants themselves can cause osmotic damage to the cell during their addition and removal. During cryoprotectant addition the cells and tissues undergo shrinkage and during removal they undergo swelling. The cryoprotectant removal process and associated cell swelling is particularly damaging. It is also the final step in the series of steps involved in the cryopreservation process and the one most often carried out in a clinical setting (e.g., operating room or emergency room). Therefore the process used for cryoprotectant removal must: (1) provide relatively rapid removal of the cryoprotectant, (2) provide a "closed" system to avoid potential contamination of the preparation, (3) be relatively simple to conduct and (4) require minimal specialized laboratory equipment. The present invention addresses each of these needs.

SUMMARY OF INVENTION

The present invention relates to a method of removing chemical compounds which protect cells (cryoprotectants) during low temperature preservation (cryopreservation). Typically such cryoprotectants are low molecular weight molecules such as glycerol, propylene glycol, ethylene glycol or dimethyl sulfoxide (DMSO). More particularly, this invention is directed to the use of solid phase non-toxic sorbents/adsorbent compositions (e.g., activated charcoal, synthetic resins, zeolites and hydroxyapatite) alone or in combination to irreversibly bind the cryoprotectant and thereby remove it from the extracellular medium. Therefore, when applied to the cell suspension, the sorbent activity will remove the cryoprotectants outside the cells and thereby shift the chemical potential of the cryoprotectant inside and outside the cells resulting in osmotic flow of the cryoprotectant out of the cells and into the cell medium for binding to the sorbent material.

The present method differs fundamentally from all previous methods in that it (1) utilizes a solid sorbent composition to remove the cryoprotectant from a cryopreserved cell suspension (and the cells) and (2) reduces the potential of osmotic damage (cell swelling) since the cryoprotectant is substantially removed before the cells are contacted with water. This is in contrast to the earlier methods (e.g., Critser et al.; U.S. Pat. No. 5,700,632) where aqueous medium is used in a predetermined protocol to remove extracellular and intracellular cryoprotectant concentrations.

DESCRIPTION OF THE PREFERRED EMBODIMENTS

Figure 1:
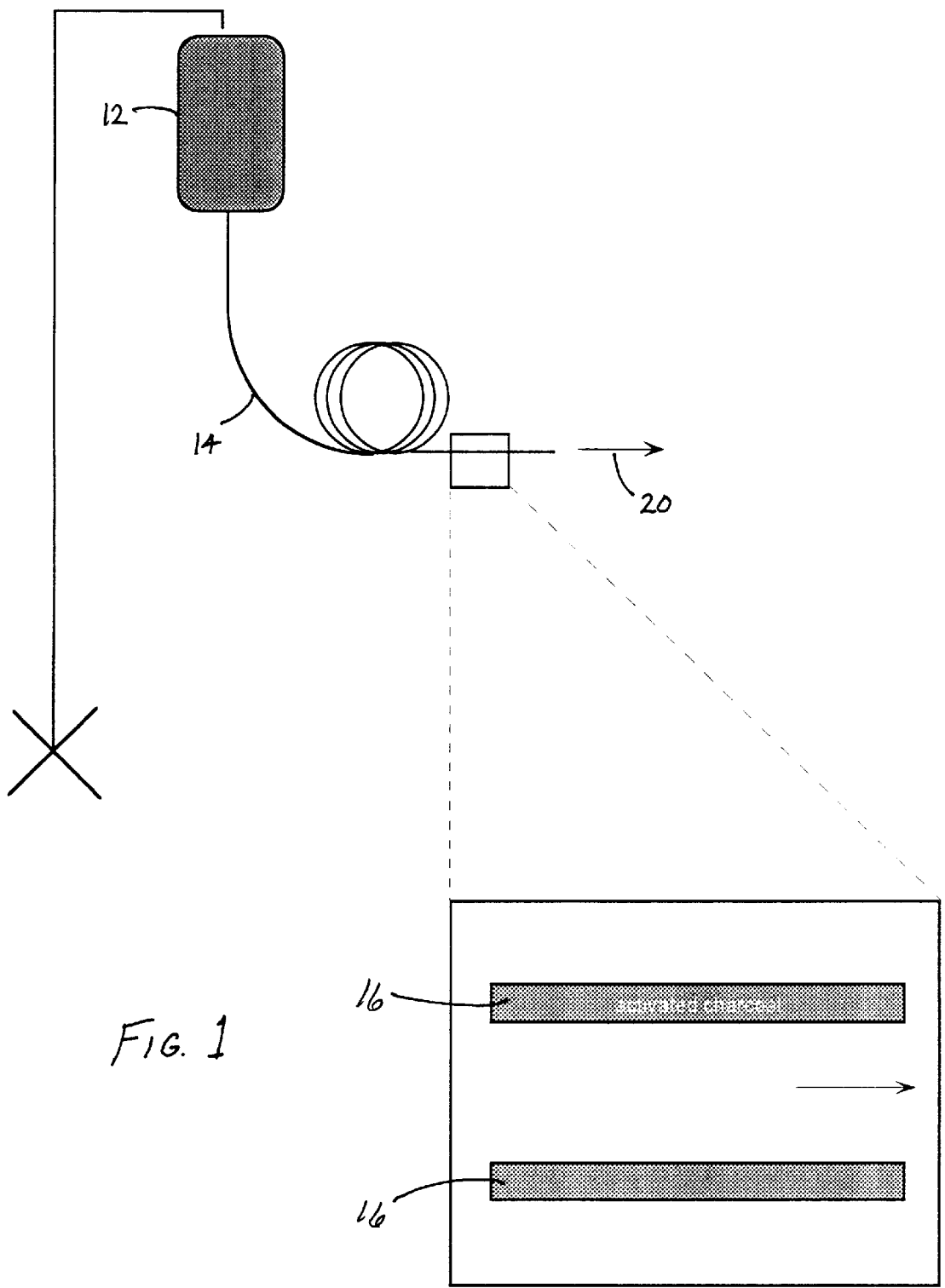
FIG. 1 illustrates use of a solid phase sorbent, activated charcoal, as a component of a tube in handling/delivery system for cryopreserved cell suspensions.

Specific language is used to describe several embodiments of this invention to promote an understanding of the invention and its principles. It must be understood that no specific limitation of the scope of this invention is intended by using this specific language. Any alteration and further modification of the described methods or devices, and any application of the principles of this invention are also intended that normally occur to one skilled in this art.

During standard equilibrium freezing methods for cryo-preserving cells and tissues, as the cell suspension is cooled to below its freeing point, ice begins to form. As ice forms in the solution surrounding the cells or tissues, electrolytes and other solutes become progressively concentrated, quickly reaching concentrations which are damaging to the cells. This solute damage is attenuated by the addition of cryoprotectant chemicals such as glycerol, propylene glycol, ethylene glycol or dimethylsulfoxide. However, the cryo-protectants themselves can cause osmotic damage to the cell during their addition and removal. During cryoprotectant addition the cells and tissues undergo shrinkage and during removal they undergo swelling. The cryoprotectant removal process and associated cell swelling is particularly damaging. It is also the final step in the series of steps involved in the cryopreservation process and the one most often carried out in a clinical setting (e.g., operating room or emergency room). Therefore the process used for cryoprotectant removal must: (1) provide relatively rapid removal of the cryoprotectant, (2) provide a "closed" system to avoid potential contamination of the preparation, (3) be relatively simple to conduct and (4) require minimal specialized laboratory equipment.

Previous methods to avoid cell damage during the cryoprotectant removal process developed by Critser et al. (U.S. Pat. No. 5,700,632) utilized measurement of the osmotic tolerance limits of cells, predetermination of cell specific plasma membrane permeability coefficients, in combination with non-equilibrium thermodynamic mathematical modeling to predict optimal methods for step-wise removal of cryoprotectants from cells. The fundamental basis for that approach is that as non-cryoprotectant solution is step-wise added to a cell suspension equilibrated with a given cryoprotectant concentration, the cells will, upon each solution addition step, undergo a given amount of cell swelling. Knowing the extent of this swelling and the maximal tolerated swelling, one can formulate the specific amount and rate of solution addition which will result in optimal cell survival at a maximal cryoprotectant removal rate. However, this method requires expensive determination of each cell's membrane permeability coefficients, large volumes of non-cryoprotectant containing media to wash and remove the cryoprotectants from the cells and trades-off cell survival for maximal cryoprotectant removal rate. Removal rate is a critical factor in allowing cells and tissues to be practically utilized in many clinical settings (e.g., emergency blood transfusions).

The present invention addresses these short-comings by utilizing a novel approach wherein the cryoprotectant is removed from cryopreserved cells and tissues by using non-toxic, biocompatible solid phase adsorbent materials to adsorb and bind the cryoprotectant component and to remove it first from the solution surrounding the cells and tissues and then (through maintenance of chemical equilibrium by osmotic flow) from intracellular space.

The adsorbent composition is typically in the form of porous particles exhibiting high surface area. They function to absorb the cryoprotectant from the liquid phase in contact with their surface. The cryoprotectant is bound to the adsorbent composition as it is removed from the liquid phase with concomitant reduction in the chemical potential (concentration) of the cryoprotectant (lowered on the outside of the cell). With the reduction of the cryoprotectant concentration on the outside of the cell, intracellular cryoprotectant concentrations are such that the cryoprotectant will equilibrium (re-establish an equal chemical potential or concentration), lowering the cryoprotectant concentration inside the cell (i.e., removing the cryoprotectant from the cell). This is a continuous process with the rate determined primarily by the affinity of the cryoprotectant for the adsorbent composition, the surface area of the composition, the temperature of the cell medium, and the volume of sorbent concentration utilized in processing the cryopreserved cell suspension. Therefore, when a faster rate is required, more adsorbent can be added to the cell suspension solution. Unlike the earlier method of Critser et al., the risk of cell swelling can easily be managed. By adding a large molecular weight substance with a low affinity for the adsorbing material (e.g. mannitol or dextran) to the cell suspension at empirically determined intervals, osmotic swelling due to inadvertent adsorption of other small molecular weight substances from the suspension can be precluded.

The invention utilizes principles and language developed in the area of the biochemistry. These fundamental principles are briefly described.

The process of this invention can be described in the following form:

Where A is the adsorbent material, C is the cryoprotectant chemical compound, and AC is the product of irreversibly bound cryoprotectant to the adsorbent.

With reference to FIG. 1, a cryopreserved platelet suspension in container 12 is delivered through tubing 14 fabricated to include activated charcoal 16 for high surface area contact with the platelet solution as it passes through the tube to remove at least a portion of the cryoprotectant and produce a cell suspension 20 having a reduced cryopreserved concentration. The method can be repeated in two or more steps as may be necessary to reduce cryoprotectant concentrations to acceptable levels.

Figure 2:
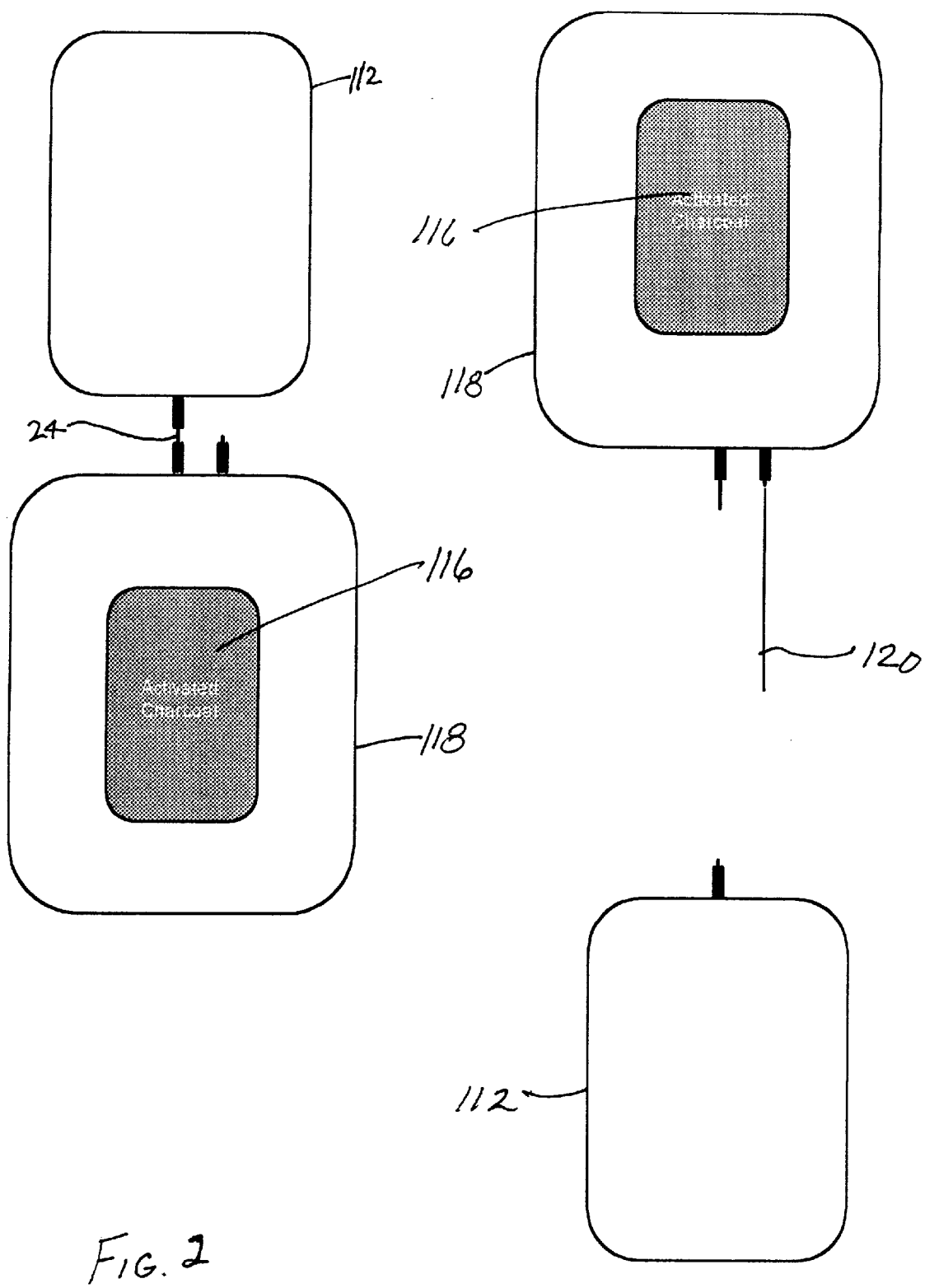
FIG. 2 is similar to FIG. 1 and illustrates an embodiment of the invention where the solid phase sorbent is bound to or forms part of the inner wall of a vessel for a cryopreserved cell suspension.

With reference to FIG. 2 a cryopreserved cell suspension in container 112 is delivered through tube connection 24 to treatment container 118 containing a volume of adsorbent composition 116 optionally bound to the wall of the container or itself contained in a semipermeable membrane structure for adsorption of the cryoprotectant. The cell suspension is held in container 118 for a period of time sufficient to allow reduction of the cryoprotectant concentration to acceptable levels for subsequent delivery through tube 120 to a patient or another temporary cell suspension storage container. Cell suspension container 112 can then be separated from treatment container 118 at connection 24.

The method in accordance with another embodiment of this invention can be carried out utilizing devices, general methods, and sorbent compositions described in U.S. Pat. Nos. 5,277,820; 4,661,246; 4,581,141, and 4,348,283, the disclosure of each being expressly incorporated herein by reference.

EXAMPLES

Example 1
Use of Charcoal to Remove Glycerol from Cells in a Single Step Process Charcoal, more particularly, activated charcoal, will irreversibly bind glycerol, a commonly used cryoprotectant chemical compound. By adding charcoal to glycerolized cell suspension, glycerol will bind to the charcoal and be removed from the solution and from the intercellular compartment.

Many cells, such as red blood cells, used widely in transfusion medicine are cryopreserved using 1–3 M concentrations of glycerol. One of the major rate limiting factors using current protocols for freezing red blood cells, is the time it takes to remove the glycerol from the cells before they can safely be transfused into a patient. This is because, using standard washing approaches for glycerol removal, the red cells will undergo extreme swelling and lyse unless the washing procedure is performed very slowly. Currently it takes approximately 1 hour to deglycerolize one unit of blood, which is far too long a time for emergency situations. Based upon the biochemical kinetic characteristics of glycerol-charcoal binding, it is possible to calculate the rate removal from solution. Using this information, it is possible to determine the optimal amount of charcoal used which will result in glycerol removal fast enough to provide a practical method for deglycerolizing red blood cells.

Experimental Validation of Method: Reduction to Practice

Rationale: The fundamental premise of this procedure is that glycerol, when used as a cryoprotectant solute, will bind to a sorbent material. This reaction will lower the chemical potential (concentration) of glycerol in the extracellular solution with concomitant osmotic transport of intracellular glycerol out of the cell.

Experiment 1: Charcoal binding of Glycerol: Charcoal (0.5 ml powdered material) was added to a 1 ml sample consisting of distilled water and 0.5 M glycerol (572 milli-Osmolal [mOsm]). The resulting charcoal/water/glycerol preparation was placed on a sample rocker for 15 minutes, centrifuged to remove the charcoal and the osmolality of the solution determined. The osmolality was reduced to 437 mOsm., or to 76% of the original value. These data demonstrate that charcoal will bind glycerol. Longer exposure times and/or increased surface area of the charcoal material (e.g., a cartridge configuration through which the solution will pass) can be used for efficient glycerol removal.

Example 2
Use of Charcoal to Remove 1,2-Propanediol or Ethylene Glycol from Cells in a Single Step Process As with glycerol, charcoal will irreversibly bind 1,2-propanediol (also called propylene glycol [PG]) and ethylene glycol [EG], which are also commonly used cryoprotectant compounds. By adding charcoal to a cell suspension, the propylene glycol or ethylene glycol will bind to the charcoal and be removed from the solution and from intracellular regions.

Many cells, such as human embryos, used widely in reproductive medicine are cryopreserved using 1–2 M concentrations of propylene glycol. As with the glycerol case and red blood cells, one of the major rate limiting factors using current protocols for utilizing embryos, is the time it takes to remove the cryoprotectants from the cells before they can safely be transfused or transplanted into a patient. This is because, using standard washing approaches for cryoprotectants, the cells will undergo extreme swelling and lyse unless the washing procedure is performed very slowly. This causes a significant loss in both efficiency and efficacy. Efficiencies are reduced due to the long time required to prepare the cell or tissue and efficiencies are reduced because this removal process is a major source of cell death during the entire cryopreservation process. However, this invention will address both these issues and improve efficiencies and efficacy.

Ethylene glycol is commonly used in the cryopreservation of cells such as human spermatozoa, and cattle embryos due to its high permeability coefficients. In some cases, the adverse osmotic events of ethylene glycol during removal are minimal because of these high membrane permeability characteristics. However, ethylene glycol is hepatotoxic (toxic to the liver) and therefore must often be removed from the sample being transfused or transplanted to ensure the safety of the patient receiving treatment. This is particularly true in veterinary patients (such as dogs) which are exquisitely sensitive to ethylene glycol toxicity.

Based upon the biochemical kinetic characteristics of propylene glycol-charcoal and ethylene glycol-charcoal binding, it is possible to calculate the rate removal from solution. Using this information, it is possible to determine the optimal amount of charcoal used which will result in cryoprotectant removal fast enough to provide a practical method for quickly and safely using cells cryopreserved with either propylene or ethylene glycol.

Experimental Validation of Method: Reduction to Practice

Rationale: The fundamental premise of this procedure is that PG and EG, when used as cryoprotectant solutes will bind to a sorbent material. This reaction will lower the chemical potential of PG or EG in the extracellular solution causing intracellular PG or EG to move out of the cell.

Experiment 2: Charcoal binding of Propylene glycol and ethylene glycol: Charcoal (0.5 ml powdered material) was added to a 1 ml sample consisting of distilled water and 0.5 M PG and EG glycerol (424 and 490 mOsm; respectively). The resulting charcoal/water/cryoprotectant preparation was placed on a sample rocker for 15 minutes, centrifuged to remove the charcoal and the osmolality of the solution determined. The osmolality was reduced to 331 (78%) and 424 (86%) for PG and EG; respectively. These data demonstrate that charcoal will bind both PG and EG. Longer exposure times and/or increased surface area of the charcoal material (e.g., a cartridge configuration through which the solution will pass) can be used for efficient PG and EG removal.

Example 3
Use of Charcoal to Remove Dimethyl Sulfoxide (DMSO) from Cells in a Single Step Process Another chemical compound typically used as a cryoprotectant is DMSO. This cryoprotectant is used for the cryopreservation of bone marrow cells (for bone marrow transplantation), and many other cell and tissue types. As with the above examples, charcoal can be used to bind and remove this chemical from the cells after freezing and warming.

Rationale: The fundamental premise of this procedure is that DMSO, when used as a cryoprotectant solute will bind to a sorbent material. This reaction will lower the chemical potential of the solute in the extracellular solution causing intracellular DMSO to move out of the cell.

Experiment 3: Charcoal binding of DMSO: Charcoal (0.5 ml powdered material) was added to a 1 ml sample consisting of distilled water and 0.5 M DMSO (492 mOsm). The resulting charcoal/water/DMSO preparation was placed on a sample rocker for 15 minutes, centrifuged to remove the charcoal and the osmolality of the solution determined. The osmolality was reduced to 397 (80%). Subsequent exposures to fresh charcoal in the same manner reduced the solution osmolality to 253 (51%) and then 100 (20%) mOsm/kg. These data demonstrate that charcoal will bind DMSO. Longer exposure times and/or increased surface area of the charcoal material (e.g., a cartridge configuration through which the solution will pass) can be used for efficient DMSO removal.

Further Aspects of this Invention

In all cases it will be necessary or desirable to remove the adsorbent material and the bound cryoprotectant from the solution containing the cells or tissues before they are used. A further aspect of this invention is the use of specific device design components for this type of removal and/or sequestration of the sorbent and the cryoprotectant compounds. The following specific design aspects are included:

Solid Phase Sorbents: One solid phase configuration would involve the binding or sequestration of the sorbent material to the tubing or other transfer conduit from the storage vessel (e.g., blood bag) to the patient or to other vessel for further processing (e.g., centrifugation tube). For example, in the case of red cell transfusion, the sorbent material might be bound or sequestered to the wall of the transfusion tube (connecting the blood bag to the patient). In this particular example the tubing could have an inner and outer wall with the sorbent material sequestered between these. The inner wall would have a porous surface, e.g., a semipermeable membrane, which would allow the extracellular solution to pass through and then over the sorbent material, while the cells were isolated within the inner passageway. This configuration is shown in FIG. 1.

Another solid phase configuration would involve the adsorbent material(s), required for the particular cryoprotectant removal process from cells, to be either chemically bound or physically adhered to the inner wall of the storage vessel (e.g., the inner wall of a plastic blood bag). In this type of system the sorbent material will be sequestered, i.e., in a separate semipermeable membrane compartment, in the container and never enter into solution. This approach will allow retention of the sorbents when the cells are removed for use. Depending upon the surface area of the cell or tissue vessel, more surface area may be required to bind all of the sorbent material(s). This configuration is shown in FIG. 2.

A third solid phase configuration involves the bonding of the sorbent material(s) to metallic (magnetic) particles. When the reaction is complete a magnet is applied to the bottom of the vessel containing the cell or tissues and the particles are drawn to the magnet. The cell or tissue suspension can then be poured off retaining the metallic particles at the source of the magnet.

While the invention has been described in detail, the same is to be considered as illustrative and not restrictive in character, it being understood that only the preferred embodiment has been described and that all changes and modifications that come within the spirit of the invention are desired to be protected.

We claim:

1. A method for removing cryoprotectant from a suspension of animal cells in a cryoprotectant-containing solution, said method comprising the steps of:

contacting the suspension with a sorbent composition capable of binding the cryoprotectant in the solution for a period of time sufficient for the cryoprotectant in the solution to bind to the sorbent composition and lower the concentration of the cryoprotectant in the solution and the suspended cells; and separating the sorbent composition which has bound cryoprotectant from the suspension.

2. The method of claim 1 wherein the rate of removal of cryoprotectant from solution is controlled by adjusting solvent selection, sorbent concentration or volume, sorbent surface area, temperature of the cell suspension, or by a combination thereof.

3. The method of claim 1 wherein the sorbent composition is either free in suspension or bound to a solid support.

4. The method of claim 1 wherein the sorbent composition comprises a solid support and a magnetic component.

5. The method of claim 1 wherein the cryoprotectant is selected from the group consisting of glycerol, 1,2-propanediol, ethylene glycol and dimethysulfoxide.

6. The method of claim 1 wherein said cells are red blood cells.

7. The method of claim 1 wherein said cells are platelets.

8. The method of claim 1 wherein said cells are hematopoietic stem cells.

9. The method of claim 1 wherein said cells are granulocytes.

10. The method of claim 1 wherein said cells are pancreatic islets or islet cells.

11. The method of claim 1 wherein said cells are oocytes.

12. The method of claim 1 wherein said cells are embryos.

13. The method of claim 1 wherein said cells are ovarian cells.

14. The method of claim 1 wherein said cells are testicular cells.

* * * * *